(12) United States Patent
Farley et al.

(10) Patent No.: US 11,172,966 B2
(45) Date of Patent: Nov. 16, 2021

(54) BONE TRANSPORT NAIL

(71) Applicant: Smith & Nephew, Inc., Memphis, TN (US)

(72) Inventors: Daniel Farley, Memphis, TN (US); Haden Janda, Germantown, TN (US); Paul Bell, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 189 days.

(21) Appl. No.: 16/473,961

(22) PCT Filed: Dec. 28, 2017

(86) PCT No.: PCT/US2017/068668
§ 371 (c)(1),
(2) Date: Jun. 26, 2019

(87) PCT Pub. No.: WO2018/125980
PCT Pub. Date: Jul. 5, 2018

(65) Prior Publication Data
US 2019/0336183 A1    Nov. 7, 2019

Related U.S. Application Data

(60) Provisional application No. 62/440,673, filed on Dec. 30, 2016.

(51) Int. Cl.
*A61B 17/72* (2006.01)
*A61B 17/84* (2006.01)
*A61B 17/86* (2006.01)

(52) U.S. Cl.
CPC ........ *A61B 17/7216* (2013.01); *A61B 17/846* (2013.01); *A61B 17/86* (2013.01)

(58) Field of Classification Search
CPC .......................... A61B 17/7216; A61B 17/846
(Continued)

(56) References Cited

U.S. PATENT DOCUMENTS

| 2008/0108995 A1 | 5/2008 | Conway et al. |
| 2009/0254088 A1* | 10/2009 | Soubeiran .......... A61B 17/7216 606/63 |

(Continued)

FOREIGN PATENT DOCUMENTS

| DE | 102011053638 A1 | 3/2013 |
| DE | 102014112573 A1 | 3/2016 |
| FR | 2949662 A1 | 3/2011 |

OTHER PUBLICATIONS

International Search Report and Written Opinion for International Application No. PCT/US2017/068668 dated May 11, 2018, 9 pages.

*Primary Examiner* — Eduardo C Robert
*Assistant Examiner* — Tara Rose E Carter
(74) *Attorney, Agent, or Firm* — Kacvinsky Daisak Bluni PLLC

(57) ABSTRACT

An intramedullary bone transport nail configured for axial bone segment transport by an externally applied magnetic field includes a nail body defining an internal chamber; locking portions for locking respective ends of the nail body in first and second bone fragments of a long bone, respectively; and a transport carriage assembly that is arranged in an axially movable manner within the internal chamber of the nail body and has an aperture for accommodating a transport bone segment screw for fixing a middle bone segment of the long bone to the bone transport carriage. The nail body defines an elongated longitudinal opening to allow axial motion of the transport bone segment screw as the transport carriage assembly moves axially by rotation of a threaded rod affixed to a magnetic driver. Rotation of the (Continued)

threaded rod is achieved by application of torque to the magnetic driver by a rotating external magnetic field.

14 Claims, 8 Drawing Sheets

(58) Field of Classification Search
USPC .................................................. 606/62–68
See application file for complete search history.

(56) References Cited

U.S. PATENT DOCUMENTS

| | | | |
|---|---|---|---|
| 2012/0179215 A1* | 7/2012 | Soubeiran | A61B 17/7216 606/86 R |
| 2013/0072932 A1* | 3/2013 | Stauch | A61B 17/7241 606/63 |
| 2014/0052134 A1* | 2/2014 | Orisek | A61B 17/7216 606/63 |
| 2014/0114311 A1 | 4/2014 | Pool et al. | |

* cited by examiner

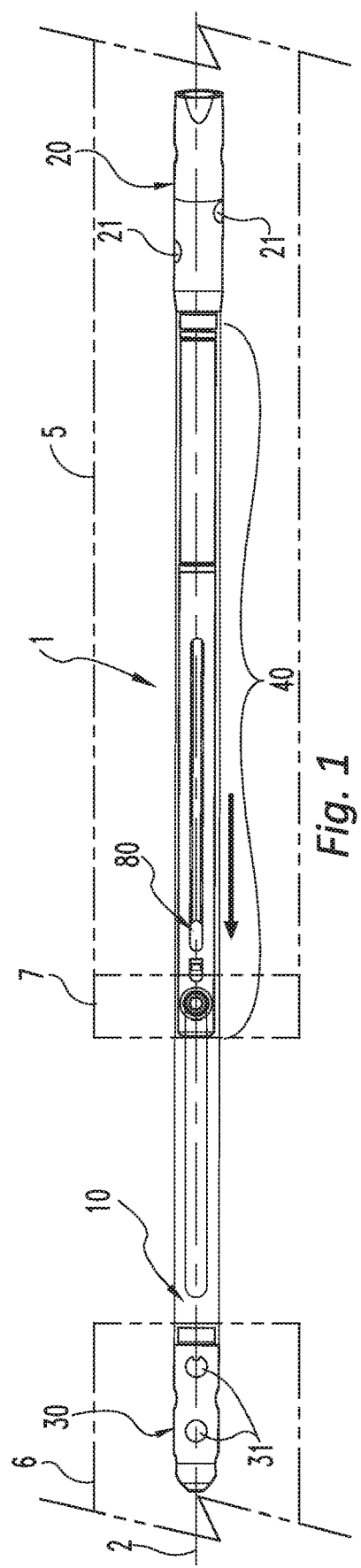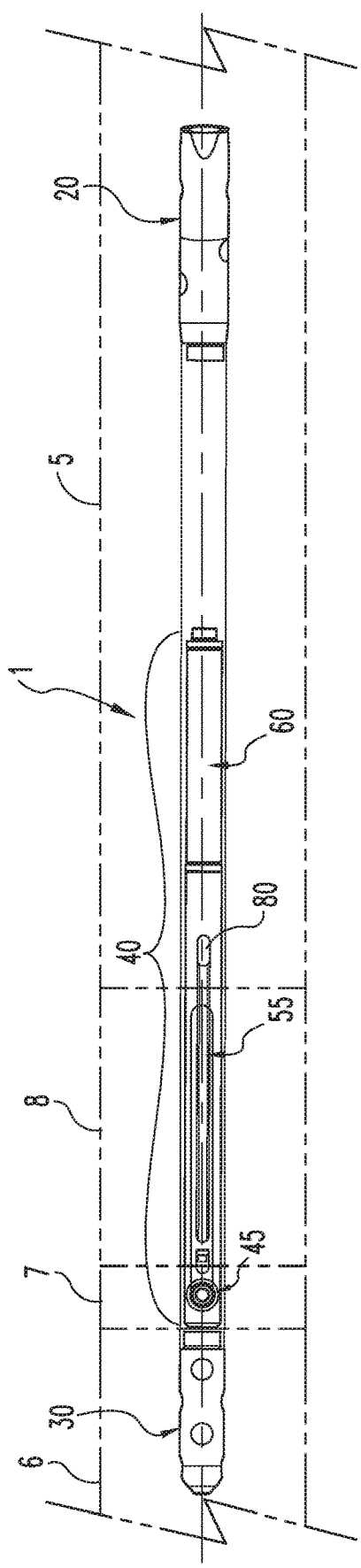

BONE TRANSPORT NAIL

CROSS REFERENCE TO RELATED APPLICATIONS

The present application is a United States National Phase filing of International Application No. PCT/US2017/068668, filed Dec. 28, 2017, which claims the benefit of U.S. Provisional Application Ser. No. 62/440,673, filed Dec. 30, 2016, the contents of which are incorporated herein by reference in their entirety.

TECHNICAL FIELD

The present disclosure generally relates to implantable bone transport devices, and more particularly, to bone transport nails that utilize an externally applied magnetic field to actuate a bone transport mechanism to direct the growth of regenerate bone tissue across a gap, thus connecting the proximal and distal segments of a long bone.

BACKGROUND

Severe trauma, infection, non-union, osteosarcoma and other morbidities of the long bones are sometimes treated by resection of the affected bone segment. Bone transport is a procedure that directs the growth of regenerate tissue across the bone gap, connecting the proximal and distal fragments. In a bone transport procedure, two bone fragments, a distal end fragment and a proximal end fragment, are held in a displaced relationship to each other by means of a medullary pin or nail fixed in the medullary canal of each bone fragment. A middle bone segment, which also originates from the same original bone tissue as the two bone fragments, is positioned adjacent a first one of the two bone fragments. At a contact site between the middle bone segment and the first one of the end bone fragments, bone tissue grows as a result of normal physiological bone healing processes. Regenerate bone thereafter continues to form in a longitudinal direction relative to the medullary canal by displacement of the middle bone segment toward the second one of the two bone fragments at a prescribed rate of translation of the middle segment, i.e., a rate that is sufficiently slow to allow bone regeneration to take place. Such bone transport processes enable a treatment of major bone defects, such as defects of more than 3 cm, such as may occur, for example, as a result of surgical resection or high trauma fractures.

Bone transport procedures can be conducted with external fixation systems that rely on tissue penetrating pins and wires. Such systems, however, can cause infection and are, at times, poorly tolerated by patients. For this reason, a fully implantable transport nail, which not only holds the first and second bone fragments in fixed positions relative to one another, but also displaces the middle bone segment at a prescribed rate and/or a prescribed interval, is preferred to provide patients a less invasive means of treatment. While various transport nail devices and actuation systems have been described that are fully implantable and that have various mechanisms for driving displacement of the middle bone segment non-invasively, a need remains for further improvements in the technological field of bone transport devices, systems and processes. The present disclosure addresses this need.

SUMMARY

In one aspect, the disclosure provides an IM bone transport nail that is configured for axial bone segment transport actuated by an externally applied magnetic field. The IM bone transport nail includes a nail body defining an internal chamber that extends along a longitudinal axis of the IM bone transport nail; a proximal locking portion for locking a first end of the nail body in a first bone fragment of a long bone; a distal locking portion for locking a second end of the nail body in a second bone fragment of the long bone; and a transport carriage assembly that is axially translatable within the internal chamber of the nail body. In one embodiment, the transport carriage assembly includes a carriage body defining at least one radially oriented aperture aligned with the elongated longitudinal opening in the nail body, the radially oriented aperture configured to receive a transport bone segment screw for fixing a middle bone segment of the long bone to the transport carriage assembly. The transport carriage assembly also includes a threaded rod coupled to the carriage body such that the threaded rod is rotatable relative to the carriage body and a magnetic driver configured to be non-invasively actuated by a moving magnetic field, the magnetic driver coupled to the threaded rod such that rotation of the magnet drives rotation of the threaded rod. The IM bone transport nail also includes a threaded block affixed to the nail body, the threaded block defining a threaded bore therethrough, through which the threaded rod of the transport assembly is configured to pass in threaded engagement with the threaded bore such that rotation of the threaded rod relative to the threaded block causes relative axial movement between the transport carriage assembly and the nail body to translate the transport carriage assembly axially along the internal chamber of the nail body. The nail body also defines an elongated longitudinal opening to allow a desired range of axial motion of the transport bone segment screw as the transport carriage assembly moves axially by rotation of the threaded rod affixed to a magnetic driver and engaged with a threaded block affixed to the nail body. Rotation of the threaded rod is achieved by application of torque to the internal device magnet by a rotating external magnetic field. In one embodiment, the carriage body defines an axial bore configured for passage of the threaded rod and a longitudinally elongated slot along at least a portion of the carriage body for passage of the threaded block as the transport carriage assembly translates relative to the nail body.

BRIEF DESCRIPTION OF THE FIGURES

FIG. 1 is a plan view of one embodiment of an IM bone transport nail according to the present disclosure, which includes a nail body and an axially translatable transport carriage assembly with the transport carriage assembly in an initial position, also with bone segments depicted schematically for context.

FIG. 2 is a plan view of the IM bone transport nail embodiment depicted in FIG. 1, with the transport carriage assembly in a different position after completed segment transport, also with bone segments and regenerate bone depicted schematically for context.

Figure 3:
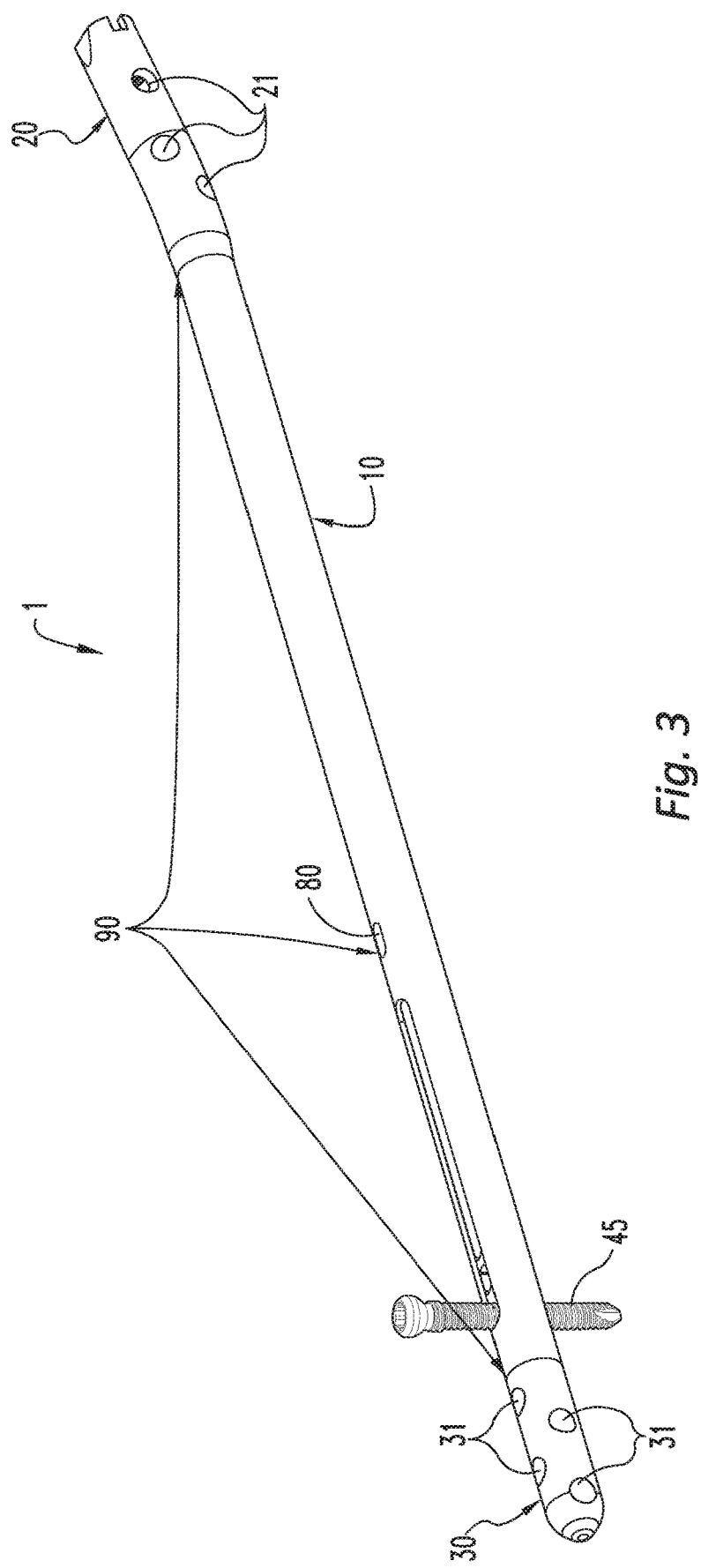
FIG. 3 is a perspective view of the IM bone transport nail embodiment depicted in FIG. 1
Figure 4:
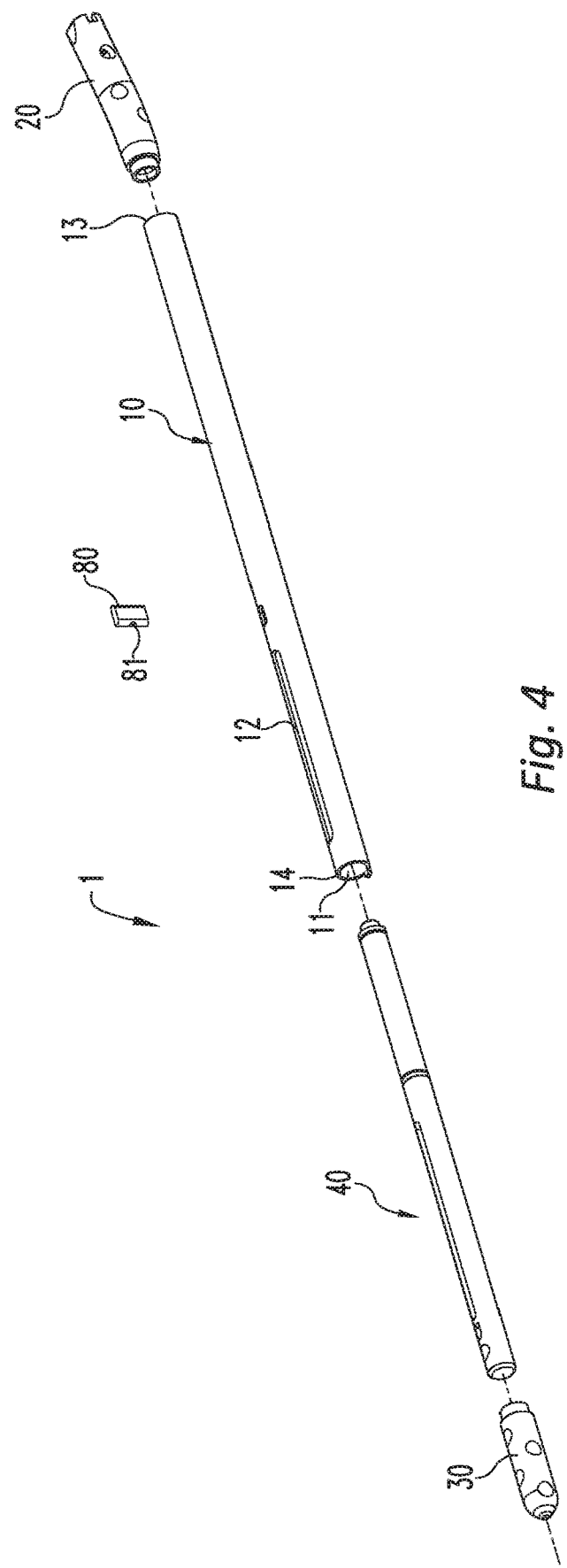
FIG. 4 is an exploded perspective view of the IM nail embodiment shown in FIGS. 1-3.
Figure 5:
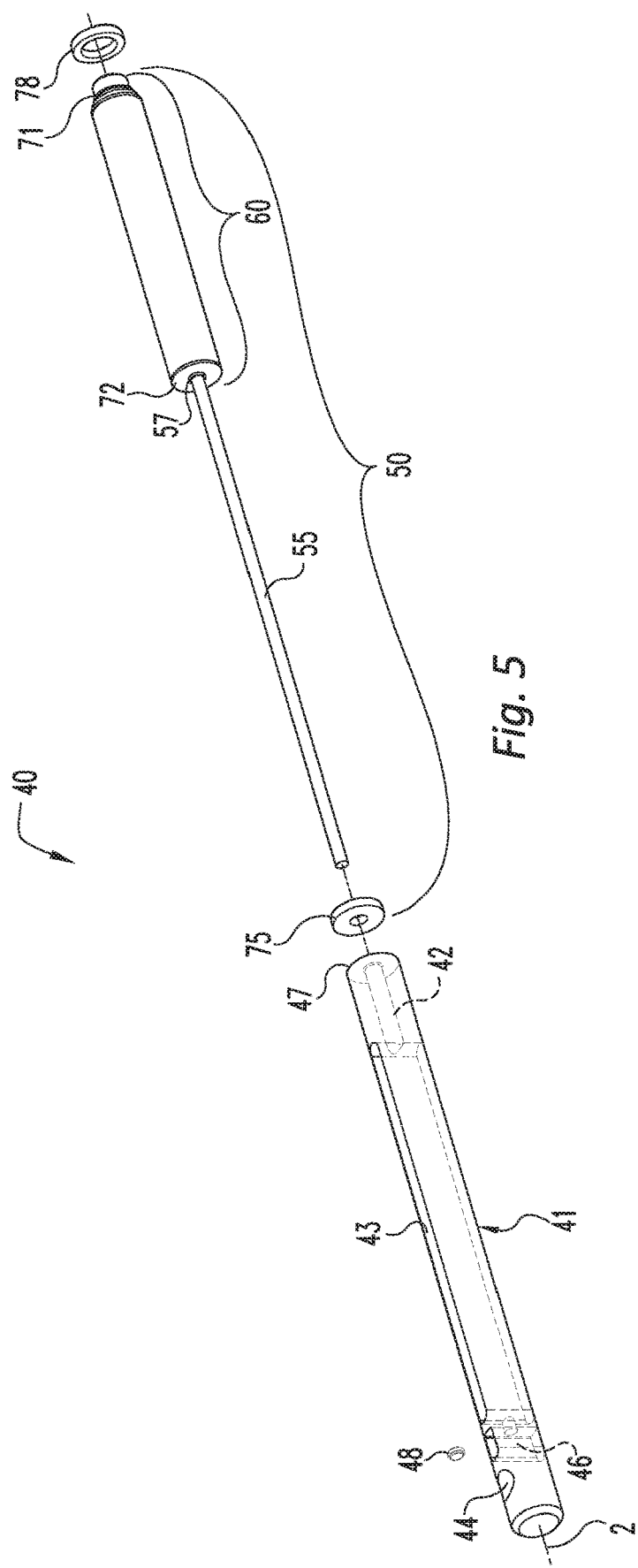
FIG. 5 is an exploded perspective view of the carriage assembly of the embodiment shown in FIG. 4.
Figure 6:
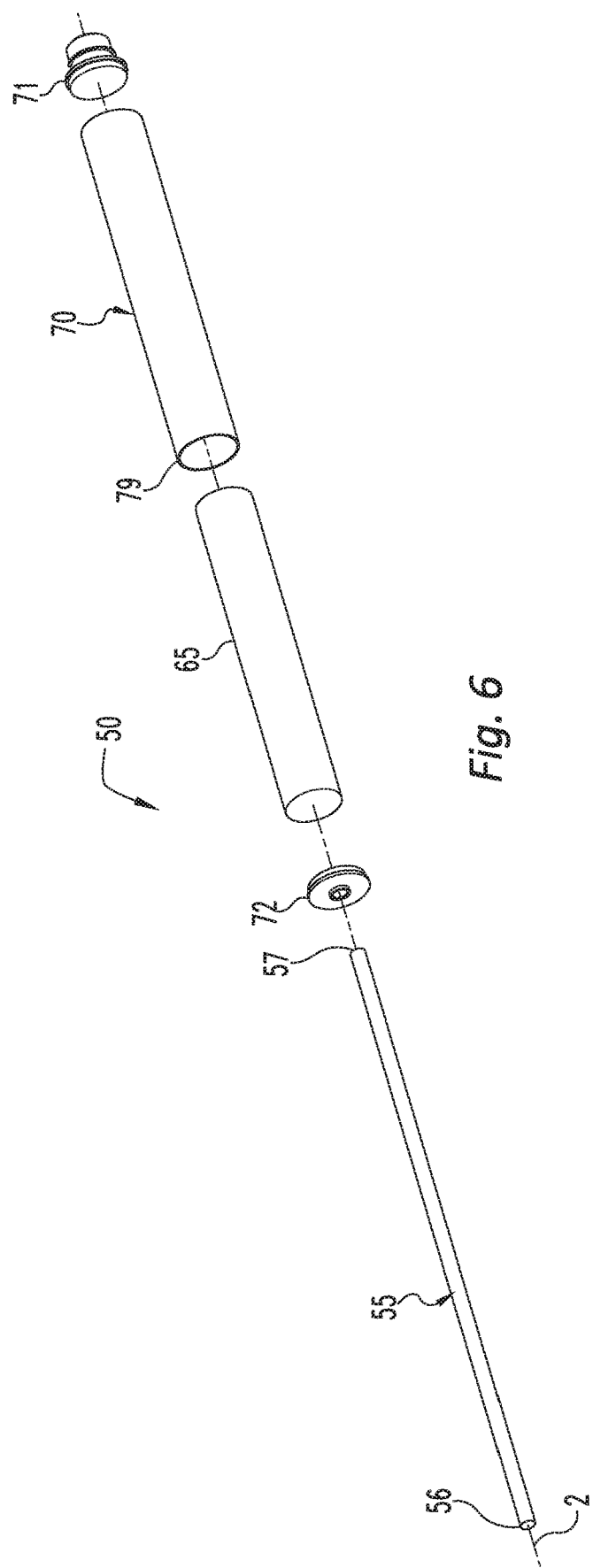
FIG. 6 is an exploded perspective view of the magnet housing assembly of the embodiment shown in FIG. 5.
Figure 7:
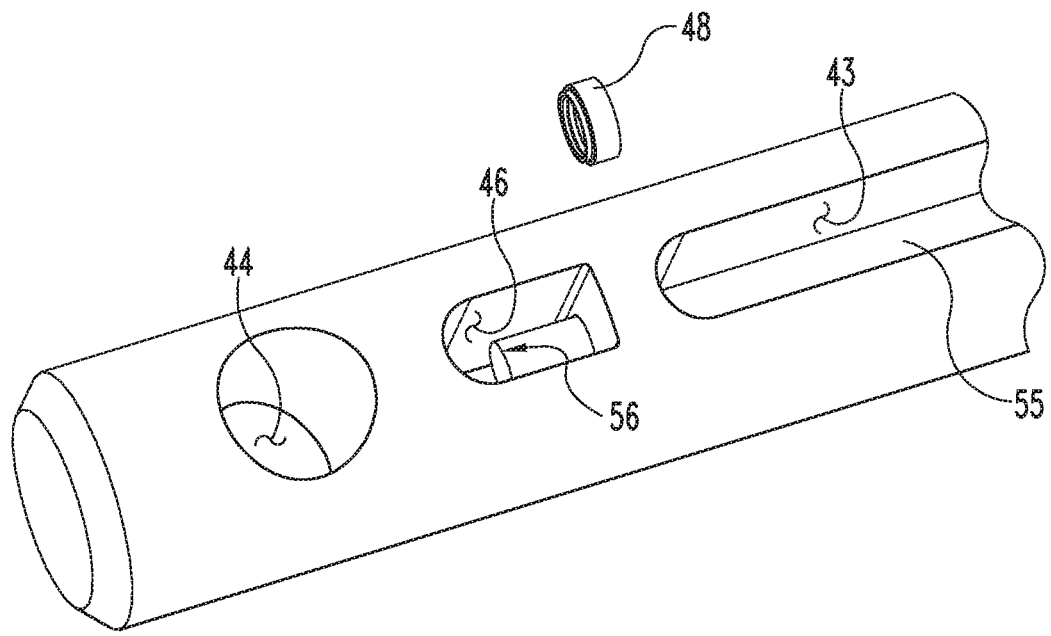
FIG. 7 is an enlarge perspective view of the distal end of the carriage body embodiment shown in FIG. 5 with the distal end of the threaded rod extending into the access slot and depicting the distraction screw nut prior to being threaded onto the distal end of the threaded rod.
Figure 8:
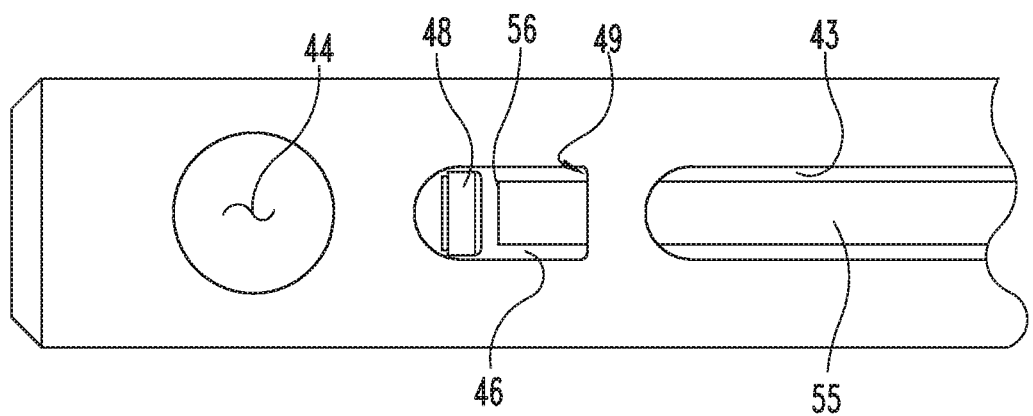
FIG. 8 is an enlarge plan view of the distal end of the carriage body embodiment and related parts as shown in FIG. 7.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein.

DETAILED DESCRIPTION OF ILLUSTRATED EMBODIMENTS

For the purposes of promoting an understanding of the principles of the invention, reference will now be made to the embodiments illustrated in the figures and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Intramedullary (IM) bone transport nail 1 depicted in FIGS. 1-8 includes proximal locking portion 20 configured for fixation in a first bone fragment 5, distal locking portion 30 configured for fixation in a second bone fragment 6 and nail body 10 extending between proximal locking portion 20 and distal locking portion 30. IM bone transport nail 1 is configured for use, for example, where the gap in which bone is to be regenerated is located in a proximal femoral or distal tibial location. Each of proximal locking portion 20 and distal locking portion 30 includes a plurality of fastener openings structured to receive fasteners for coupling each of the proximal locking portion 20 and distal locking portion 30 to respective first and second bone fragments of a patient. In the embodiment shown, first and distal locking portions 20, 30 define first openings 21 and second openings 31, respectively, positioned roughly perpendicular to the longitudinal axis 2 of IM bone transport nail 1 and configured to receive fixation elements, such as, for example, locking screws or bolts (not shown) to anchor proximal and distal locking portions 30, 40 in the first and second bone fragments, respectively.

Nail body 10 of IM bone transport nail 1 is roughly cylindrical and is at least partially hollow to accommodate transport carriage assembly 40. Nail body 10 defines an internal chamber 11 configured to receive and retain transport carriage assembly 40 in an axially slidable arrangement. Internal chamber 11 of nail body 10 and transport carriage assembly 40 are dimensioned such that transport carriage assembly 40 is able to translate axially within nail body 10. Nail body 10 also defines elongated longitudinal opening 12 that opens diametrically out on opposite sides of nail body 10 at an axial position corresponding to the axial range of motion desired for movement of transport bone segment screw 45 that is affixed to middle bone segment 7 in normal use of IM bone transport nail 1. Middle bone segment 7 is situated between first bone fragment 5, which typically is a first end of a long bone, and second bone fragment 4, which typically is a second end of a long bone. In alternate embodiments, first bone fragment 5 can be a proximal bone fragment or a distal bone fragment. For example, IM bone transport nail 1 is well suited for a bone transport procedure to regenerate bone for repair of a proximal femoral or distal tibial defect. When IM bone transport nail 1 is used for repair of a proximal femoral defect, first bone fragment 5 is a distal end fragment of a femur and second bone fragment 6 is a proximal end fragment of the femur. When IM bone transport nail 1 is used for repair of a distal tibial defect, first bone fragment 5 is a proximal end fragment of a tibia and second bone fragment 6 is a distal end fragment of the tibia.

Transport carriage assembly 40 includes carriage body 41, threaded rod 55 and magnetic driver 60. Threaded rod 55 is coupled to magnetic driver 60 in axial alignment. Together, threaded rod 55, magnetic driver 60 and their respective components are referred to in this embodiment as a "magnet housing assembly." Magnetic driver 60 includes an inner magnet 65, which may be accommodated in a casing or carrier to facilitate coupling of the inner magnet to threaded rod 55. In one embodiment, inner magnet 65 is hermetically sealed in a housing as described further below. The term "inner" is used herein in reference to the magnet of magnetic driver 60 to distinguish this magnet from a different magnet or multiple different magnets employed by an external actuator as described in greater detail below, which magnet or magnets of an external actuator, are referred to as "outer magnets." As shown more clearly in FIG. 6, magnet housing assembly 50 of the embodiment shown includes inner magnet 65, magnet housing 70, first magnet housing cap 71 and second magnet housing cap 72. In the embodiment shown, inner magnet 65, magnet housing 70, first magnet housing cap 71, second magnet housing cap 72 and threaded rod 55 are assembled and coupled together such that rotation of inner magnet 65 rotates the remaining elements. In one manner of assembly, for example, these components are welded together to achieve rotation of these elements together. In one embodiment, inner magnet 65 is hermetically sealed within magnet housing 70, which prevents contact of inner magnet 65 with the patient's body. Both carriage body 41 and magnet housing 70 are roughly cylindrical in this embodiment and have outer diameters that are roughly equal to the inner diameter of internal chamber 11 of nail body 10. In the embodiment shown, inner magnet 65 comprises a permanent magnet with diametrical magnetization. In other words, the poles of inner magnet 65 are perpendicular to the rotational axis of internal magnet 65. While neodymium magnets are suggested, other magnets may be employed as will be apparent to those skilled in the art.

Carriage body 41 of transport carriage assembly 40 defines a radially oriented aperture 44 in which a transport bone segment screw 45 is positionable during use of IM transport nail 1. Transport bone segment screw 45 fixes middle bone segment 7 to carriage body 41. Carriage body 41 also defines axial bore 42 and elongated slot 43.

Axial bore 42 is configured to accommodate threaded rod 55 within carriage body 41 without restricting free rotation of threaded rod 55 relative to carriage body 41. Axial bore 42 therefore has a radial dimension greater than the greatest diameter of threaded rod 55 and an axial dimension sufficient to accommodate the full length of threaded rod 55 when transport carriage assembly 40 is fully assembled for use. Upon assembly of transport carriage assembly 40 by insertion of threaded 55 into axial bore 42, bearing ring 75 is positioned between second magnet housing cap 72 and the proximal end 47 of carriage body 41 to reduce frictional forces of the assembly and enable magnet housing assembly 50 to rotate freely within nail body 10 relative to carriage body 41. Magnet housing assembly 50 in the embodiment shown also includes optional bearing ring 78 adjacent first magnet housing cap 71 to facilitate rotation of magnetic driver 60 within nail body 10. For example, the presence of optional bearing ring 78 may operate to reduce frictional forces within IM bone transport nail 1 should the proximal end of magnet housing assembly 50 come into contact with other surfaces within internal chamber 11.

To prevent separation of magnet housing assembly 50 from carriage body 41 following assembly of transport carriage assembly 40, access slot 46 is formed in carriage body 41 at a position between elongated slot 43 and radially oriented aperture 44. More particularly, access slot 46 is positioned at an axial location whereby axial bore 42 extends to and opens into access slot 46. Upon assembly of transport carriage assembly, the distal end 56 of threaded rod 55 extends into access slot 46 through axial bore 42. As discussed in greater detail below in connection with assembly of IM bone transport nail 1, when the distal end 56 of threaded rod 55 is positioned within access slot 46 during assembly, distraction screw nut 48 is threaded onto the distal end 56 of threaded rod 55 and fixedly coupled to threaded rod 55 such that further relative movement between threaded rod 55 and distraction screw nut 48 is prevented. For example, in one embodiment once distraction screw nut 48 has been threaded onto threaded rod 55, distraction screw nut 48 is spot welded to threaded rod 55 to fix its axial position relative to threaded rod 55. Following affixation of distraction screw nut 48 to threaded rod 55 as described, any applied separating force between carriage body 41 and magnet housing assembly 50 will cause distraction screw nut 48 to contact side wall 49 of access slot 46 to prevent magnet housing assembly 50 (i.e., threaded rod 55 and magnetic driver 60) from separating from carriage body 41. In the embodiment shown, the distal end 56 of threaded rod 55 at the position of distraction screw nut 48 carries no tensile load during normal use of IM bone transport nail 1 and so no bearing is included between distraction screw nut 48 and side wall 49 of access slot 46. It is contemplated, however, that other embodiments may be configured to apply a tensile load to threaded rod 55 at this junction. In such embodiments, an optional bearing ring or a bushing may be included between the distraction screw nut 48 and side wall 49 of access slot 46.

Elongated slot 43 is configured to accommodate threaded block 80, and to provide clearance relative to threaded block 80 when transport carriage assembly 40 moves axially relative to nail body 10 (to which threaded block 80 is affixed), as described in greater detail below in connection with normal operation of IM bone transport nail following implantation into a patient. While elongated slot 43 in this embodiment passes entirely through carriage body 41, which provides for threaded block to extend diametrically to both opposing sides of nail body 10, in alternative embodiments (not shown) elongated slot 43 can be formed as a groove on one side of carriage body 41 that extends only part way through carriage body 41 and opens radially out on only one side of carriage body 41. In this alternate embodiment, threaded block 80 can be affixed to nail body 10 only on one side of nail body 10. In the embodiment shown, proximal locking portion 20, nail body 10 and distal locking portion 30 are affixed to one another, and threaded block 80 is affixed to nail body 10, at welded joints 90, as depicted in FIG. 3. In alternative embodiments, proximal locking portion 20, nail body 10, threaded block 80 and distal locking portion 30 can be affixed to one another in other ways or two or more of these components can be formed as portions of a single unitary body.

Magnetic driver 60 in this embodiment is rigidly coupled to proximal end 57 of threaded rod 55. In this embodiment, magnetic driver 60 and threaded rod 55 are rotationally fixed relative to one another. Fixation of magnetic driver 60 to threaded rod 55 an be achieved by welding proximal end 57 of threaded rod 55 to second magnet housing cap 72, which is in turn welded to the distal end 79 of magnet housing 70. In this embodiment, welding of threaded rod 55 to magnetic driver 60 eliminates any degrees of rotational freedom between threaded rod 55 and magnetic driver 60. Therefore, axial rotation of magnetic driver 60 directly drives axial rotation of threaded rod 55. Other embodiments are contemplated, however, where components comprising gears or other mechanisms are incorporated into the transport carriage between inner magnet 65 and the threaded rod 55 to modify the relative rate of rotation between these two components. This may be desired, for example, to increase torque applied to the threaded rod or for other reasons. In such embodiments, rotation of inner magnet 65 drives rotation of threaded rod 55.

Threaded rod 55, at a location between proximal end 57 that is coupled to magnetic driver 60 and distal end 56 that is accommodated within access slot 46, engages threaded block 80. Threaded block 80 defines a threaded bore 81 extending through threaded block 80 along longitudinal axis 2. Threaded rod 55 includes a set of external threads that are engaged with a set of internal threads formed in the threaded bore 81 of threaded block 80. Stated alternatively, the external threads of threaded rod 55 have diameter and pitch features complementary to those of the internal threads of threaded bore 81 such that outward facing threads on threaded rod 55 properly engage inward facing threads in the threaded bore of threaded block 80. Threaded block 80 is fixed to nail body 10 so that the position of threaded block 80 is fixed with respect to nail body 10. Threaded block 80 permits rotation of threaded rod 55 relative to the nail body 10, and rotatably couples nail body 10 and threaded rod 55 to drive axial movement of transport carriage assembly 40 along longitudinal axis 2. In the embodiment shown, threaded block 80 is coupled to diametrically opposite sides of nail body 10 in an orientation whereby threaded block passes through elongated slot 43 of carriage body 41, which is positioned within internal chamber 11 of nail body 10. In this orientation, rotation of magnetic driver 60 results in rotation of threaded rod 55 within the threaded bore of threaded block 80 and, because threaded block 80 is fixed to nail body 10, rotation of the magnetic driver 60 and threaded rod 55 results in axial movement of transport carriage assembly 40 relative to nail body 10 along axis 2 of IM bone transport nail 1.

FIG. 1 illustrates the IM bone transport nail 1 with transport carriage assembly 40 located at a first position, and FIG. 2 illustrates the bone transport nail 1 with transport carriage assembly 40 located at a second position. The transport carriage assembly 40 may be moved between the first and second positions by rotating inner magnet 65 with actuation unit 200, as described more fully below. More specifically, rotation of inner magnet 65 causes rotation of threaded rod 55 and movement of the transport carriage assembly 40 along longitudinal axis 2, thereby axially adjusting the position of transport carriage assembly 40 within IM bone transport nail 1. As is evident from a comparison of FIGS. 1 and 2, the axial position of threaded block 80 with respect to nail body 10 remains unchanged and the axial positions of the magnetic driver 60, threaded rod 55 and carriage body 41 translate relative to nail body 10, but remain unchanged relative to one another. Elongated longitudinal opening 12 of nail body 10 enables transport carriage assembly 40 to move axially relative to nail body 10 with transport bone segment screw 45 affixed to middle bone segment 7 passing through elongated longitudinal opening 12.

While the present disclosure is not limited to devices or components having specific dimensions, in one embodiment IM bone transport nail 1 has a diameter of 11 mm and a length of 345 mm. The various parts of IM bone transport nail 1 other than inner magnet 65 preferably are made from a mechanically resistant biocompatible material, such as certain titanium alloys, or high-resistance chrome- and cobalt-based alloys, for example, ASTM 1058 Cobalt Chrome or ASTM F-1537 Co—Cr—Mo alloy.

In various embodiments, surfaces of the parts, and particularly surfaces that slidably engage one another, particularly under load conditions, such as, for example, external threads of treaded rod 55 and internal threads of threaded block 80, are treated to limit friction and possible wear and tear. Examples of such treatments include treatments based on amorphous diamond-like carbon or tungsten disulphide or plasma ion implantation of oxygen or nitrogen ions.

The first stage of assembling IM bone transport nail 1 from its component parts is to build magnet housing assembly 50. This is done by (i) positioning inner magnet 65 in magnet housing 70, (ii) affixing first magnet housing cap 71 to the proximal end of magnet housing 70, (iii) affixing second magnet housing cap 72 to the distal end of magnet housing 70, and (iv) rigidly coupling proximal end 57 of threaded rod 55 to second magnet housing cap 72. The components of magnet housing assembly 50 can be affixed to one another as described above by welding or other means for holding them in a fixed position relative to one another under loads and other conditions applicable during use of IM bone transport nail 1. The components are assembled in a manner such that threaded rod 55 will be in axial alignment with inner magnet 65 upon completion of magnet housing assembly 50. Coupling of threaded rod 55 to second magnet housing cap 72 can be achieved in a wide variety of ways, including threading proximal end 57 of rod 55 into a complementary tapping in the outer surface of second magnet housing cap followed by welding of the junction. It is not intended that the present disclosure be limited to this manner of coupling these components, however, as other means of coupling are contemplated.

With the magnet housing assembly complete, transport carriage assembly 40 is then assembled within internal chamber 11 of nail body 10 as follows: First, carriage body 41 is inserted into internal chamber 11 of nail body 10 such that elongated slot 43 of carriage body 41 aligns with an opening formed in nail body 10 at a predetermined axial position at which threaded block 80 is to be affixed to nail body 10. This opening is sized to closely conform with the dimensions of threaded block 80. Threaded block 80 is inserted into this opening such that threaded block extends through elongated slot 43 and such that threaded bore 81 of threaded block 80 aligns with axial bore 42 of carriage body 41. Threaded block 80, when positioned in this manner, has an outer diameter that matches the outer diameter of nail body 10 and forms a seam with outer body 10 that can be welded following completion of IM transport nail assembly to hold threaded block 80 in position relative to nail body 10. Carriage body 41 preferably is positioned such that threaded block 80 abuts the distal end of elongated slot 43. Distal end of threaded rod 55 is inserted through bearing ring 75, introduced into internal chamber 11 at proximal end 13 of nail body 10 and advanced distally until distal end 56 of threaded rod 55 enters axial bore 42 at the proximal end 47 of carriage body 41 and meets threaded bore 81 of threaded block 80 in axial alignment therewith. Threaded rod 55 then is rotated such that it advances axially through threaded bore 81 of threaded block 80, and rotation of threaded rod 55 is continued until (i) distal end 56 of threaded rod 55 passes through threaded block 80 and extends into access slot 46, and (ii) second magnet housing cap 72 fits snugly against bearing ring 75 and bearing ring 75 fits snugly against proximal end 47 of carriage body 41. With the components of transport carriage assembly 40 arranged in this manner, and with access slot 46 of carriage body 41 accessible through elongated longitudinal opening 12 of nail body 10, distraction screw nut 48 is threaded onto the distal end 56 of threaded rod 55 and spot welded to threaded rod 55 to prevent distraction screw nut 48 from separating from threaded rod 55. If desired, a bearing ring or a bushing (not shown) can be positioned on threaded rod 55 between distraction screw nut 48 and side wall 49 of access slot 46; however, in IM bone transport nail 1, such a bearing or bushing is not required because transport carriage assembly 40 is not subject to a tensile load during intended use of this embodiment. Once distraction screw nut 48 is spot welded to threaded rod 55, assembly of transport carriage assembly 40 is complete. If desired, magnet housing assembly 50 can be rotated in the reverse direction to axially move transport carriage assembly toward proximal end 13 of nail body 10 to position radially oriented aperture 44 in alignment with the proximal end of elongated longitudinal opening 12 of nail body 10.

To complete assembly of IM bone transport nail 1, optional bearing ring 78 can be positioned adjacent first magnet housing cap 71, proximal locking portion 20 is affixed to proximal end 13 of nail body 10 and distal locking portion 30 is affixed to distal end 14 of nail body 10. The following joints are then welded, such as, for example, by laser welding: joints between (i) proximal locking portion 20 and nail body 10, (ii) distal locking portion 30 and nail body 10, and (iii) threaded block 80 and nail body 10. These joints are denoted as welded joints 90 in FIG. 3. This completes the assembly of IM bone transport nail 1.

Use of IM bone transport nail 1 is indicated where a need exists for bone regrowth in a gap between two existing bone fragments, such as, for example, a gap resulting from fractures or other injuries of long bones, bone loss due to tumors, necessary resectioning or severe trauma, for example. Bones which typically would be treated with IM bone transport nail 1 include thigh bone (femur) and shin bone (tibia); however, features of this disclosure also are suitable for modifying the size and/or shape of the device to provide for treatment of the upper arm bone (humerus), ulna, radius, fibula and other long bones, and also are suitable for small stature or youthful patients, since the design is suitable for use in bones that are smaller than average adult bones. While implantation of IM bone transport nail 1 for use to regrow bone in the context of a femur or tibia is described primarily in this disclosure for convenience, the disclosure also contemplates other embodiments formed for uses in medullary canals of other long bones and at other skeletal locations other than medullary canals of long bones.

After opening and incremental reaming of the intramedullary canal of a long bone to be treated and removal of the segmental defect, (or after opening and incremental reaming of the intramedullary canals of two bone fragments between which bone regrowth is desired if a segmental defect has already been removed), one of the bone fragments is osteotomized at the level of the transport segment. IM bone transport nail 1 is implanted such that proximal locking portion 20 is affixed within the medullary canal of a first bone fragment, such as, for example a proximal tibial bone fragment; distal locking portion 30 is affixed within the medullary canal of a second bone fragment, such as, for example, a distal tibial bone fragment; and a middle segment of bone (also referred to herein as a transport bone segment), such as a portion of tibial bone cut from the proximal tibial bone fragment, is affixed to carriage body 41 of IM bone transport nail 1 as schematically shown in FIG. 1. Proximal locking portion 20 is affixed to first bone fragment 5 by positioning fixation elements, such as locking screws within first openings 21 in a manner whereby the locking screws fix proximal locking portion 20 relative to first bone fragment 5. Similarly, distal locking portion 30 is affixed to second bone fragment 6 by positioning fixation elements, such as locking screws within second openings 31 in a manner whereby the locking screws fix distal locking portion 30 relative to second bone fragment 6. By way of example, first bone fragment 5 can be a distal fragment of a femur (upper leg bone) and second bone fragment 6 can be a proximal fragment of the femur. As another nonlimiting example, first bone fragment 5 can be a proximal fragment of a tibia (lower leg bone) and second bone fragment 6 can be a distal fragment of the tibia. In one embodiment, locking screw trajectories are consistent with the existing Trigen META system. In this embodiment, existing instruments and drill guides can be used for locking screw placement. Carriage body 41 is affixed to middle bone segment 7 using transport bone segment screw 45, which may be, for example, a Trigen Screw. Fixation of the locking screws and transport bone segment screw can be accomplished using the perfect circles technique. With IM bone transport nail 1 implanted in this manner, a proximal surface of middle bone segment 7 abuts a distal surface of first bone fragment 5 as shown schematically in FIG. 1 to form an interface where bone regrowth will occur.

Following implantation of IM bone transport nail 1, and within a prescribed length of time after the implantation procedure after which bone regrowth process have begun at the interface between middle bone segment 7 and first bone fragment 5, distraction of transport carriage assembly is begun to slowly displace middle bone segment 7 away from first bone fragment 5 and toward second bone fragment 6 at a prescribed rate and/or at prescribed intervals. During this process, and provided that the speed of movement of middle bone segment 7 is sufficiently slow, regrowing bone is formed at the interface between middle bone segment 7 and first bone fragment 5, and continues to form as middle bone segment 7 slowly moves away from first bone fragment 5. Once middle bone segment 7 contacts second bone fragment 6, regenerate bone 8 is present in the original gap. Bone formation also occurs at the interface between middle bone segment 7 and second bone fragment 6, thereby completing the process of regrowing bone in the original gap between first bone fragment 5 and second bone fragment 6. Typical rates for the relative movement of transport carriage assembly during the transport process are from about 0.2 mm to about 2.5 mm per day. In other manners of practicing the method, a rate of from about 0.5 mm to about 1.5 mm per day is used. Docking of the middle bone segment and complete healing are required before removal of IM bone transport nail 1.

Displacement of transport carriage assembly as described above is achieved by rotation of threaded rod 55, which is achieved by rotation of inner magnet 65. In IM bone transport nail 1, threaded rod 55 is under tension during axial loading conditions resulting from rotation of threaded rod 55. More specifically, during rotation of threaded rod 55 and displacement of transport carriage assembly 40, the load-bearing points of contact between components are at (i) the threaded rod 55/threaded block 80 interface, (ii) the abutment of proximal end of carriage body 41 with second magnet housing cap 72 (through bearing 75), and (iii) at the junction between threaded rod 55 and second magnet housing cap 72.

When transport carriage assembly 40 is moved in a direction represented by the arrow on FIG. 1 as a result of rotation of threaded rod 55, transport bone segment screw 45 transmits a tensile force on transport bone segment 7 to which transport bone segment screw 45 is affixed, relative to first bone fragment 5. Transport bone segment screw 45 thereby exerts a compressive load on carriage body 41 via the engagement of transport bone segment screw 45 in radially oriented aperture 44. This compressive force is transmitted by carriage body 41 to second magnet housing cap 72, thereby causing tension in the portion of threaded rod 55 that extends from second magnet housing cap 72 to threaded block 80, which is fixed to nail body 10. Thus, the axial load on the threaded rod is between threaded block 80 (affixed to outer nail body 10) and the proximal end 57 of threaded rod 55 at its junction with second magnet housing cap 72. When IM bone transport nail 1 is under a compressive axial load, which it is during use, the axial load on the rod is tensile. In other words, when the transport carriage is under compression, it imparts this load to the magnet housing cap, which in turn puts a tensile load on threaded rod 55 between magnet housing cap 72 (where it is welded) and where is it threaded into locking block 80. As the carriage distracts, the length of threaded rod under tensile load decreases.

Rotation of threaded rod 55 is achieved by applying a rotational force on inner magnet 65 that overcomes opposing forces to rotate inner magnet 65. Because inner magnet 65 is fixedly contained within magnet housing 70 and second magnet housing cap 72 is fixedly coupled to magnet housing 70 and threaded rod 55, rotation of inner magnet 65 drives rotation of threaded rod 55. Rotation of inner magnet 65 is achieved by applying an appropriately positioned and oriented rotating magnetic field (also referred to herein as a magnetic driving field) of sufficient strength across inner magnet 65.

The creation of a magnetic driving field for rotating magnetic driver 60 and threaded rod 55 coupled coaxially therewith can be accomplished by a wide variety of means. In one manner of actuating rotation of magnetic driver 60 following implantation of IM bone transport nail 1 in a skeletal position of a patient, an external actuator, also referred to herein as an actuation unit is used. The external actuator is operable to position a driving magnet, also referred to herein as an outer magnet, near the implanted device, but external to the patient, at the height of the magnetic driver 60. The external actuating mechanisms are designed and positioned to maximize torque to inner magnet 65 and threaded rod 55 and, in any event, to provide sufficient torque to rotate inner magnet 65 despite the distance between inner magnet 65 and outer magnets in the actuation unit and applied resisting forces on IM bone transport nail 1. In this regard, rotation of inner magnet 65 must overcome any compressive load imparted between nail body 10 and transport carriage assembly 40 of IM bone transport nail 1 by bone tissue and other tissues of the patient.

In the presence of a magnetic driving field perpendicular to the rotational axis of inner magnet 65 (which lies on longitudinal axis 2 in this embodiment) and rotating around this axis, inner magnet 65 tends to become oriented in the magnetic driving field, which applies a torque to inner magnet 65 and causes inner magnet 65 to rotate in the same rotational direction of the magnetic driving field, together with threaded rod 55 that is coupled coaxially with inner magnet 65, if the applied torque is greater than the load torque on threaded rod 55 under the load applied to it at the time when the magnetic driving field is activated. Rotation of threaded rod 55 displaces transport carriage assembly 40 relative to nail body 10 as described above. Thus, by operating the actuator, transport carriage assembly 40 may be pushed away from first bone fragment 5, thereby transporting middle bone segment 7 away from first bone fragment 5.

In one embodiment, the driving magnet comprises at least one permanent magnet, one of the poles of which is directed towards longitudinal axis 2 that is common to nail body 10 and to magnetic driver 60. In another embodiment, an even greater torque can be applied to the magnetic driver 60 by using two permanent driving magnets positioned such that the south pole of one is facing the north pole of the other, and such that the magnetic driver and the part of the patient's body that surrounds the IM bone transport nail 1 are positioned between the two permanent magnets.

Figure 9:
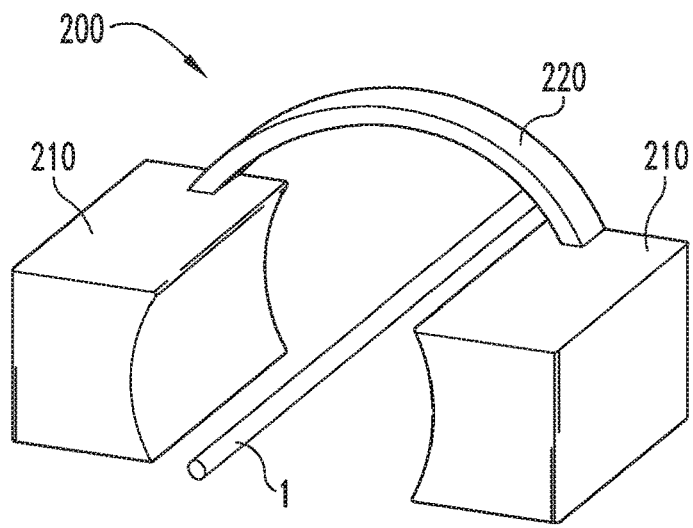
FIG. 9 is a perspective view of a system according to one embodiment that includes an IM bone transport nail and an actuating mechanism.
Figure 10:
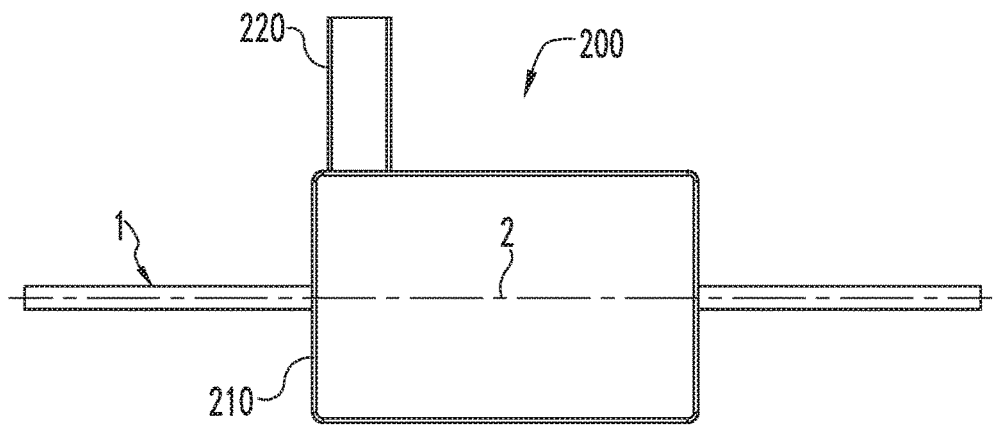
FIG. 10 is a side view of the system embodiment depicted in FIG. 9.
Figure 11:
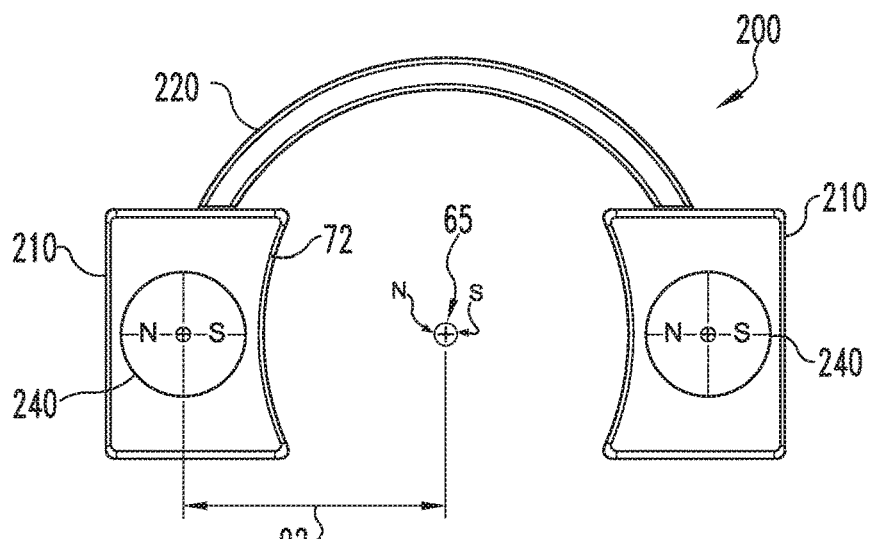
FIG. 11 is an end view of the system embodiment depicted in FIG. 9 with only the inner magnet of the IM bone transport nail shown.

In one embodiment, depicted in FIGS. 9-11, actuation unit 200 includes a pair of housings 210, an arcuate body 220 connecting the housings 210, and a pair of outer magnets 240 mounted in the housings 210. In FIGS. 9-11, actuation unit 200 is illustrated in a position in which it partially surrounds the IM bone transport nail 1, such that the outer magnets 240 are positioned on opposite sides of the inner magnet 65. Magnets 240 may, for example, be neodymium magnets. With the outer magnets 240 positioned on opposite sides of inner magnet 65, and with each of the outer magnets 240 having an inward-facing side of one polarity aligned with a side of the inner magnet having the opposite polarity, the inner magnet 65 is magnetically coupled to the actuation unit 200. Thus, rotation of the actuation unit 200 about the longitudinal axis 2 results in a torque being applied to the inner magnet 65. As a result of the torque, the inner magnet 65 rotates about the longitudinal axis 2, thereby causing rotation of the threaded rod 55, which in turn causes translation of transport carriage assembly 40 relative to nail body 10.

In certain forms, the arcuate body 220 may include an adjustment device which permits relative movement of the housings 210 in a direction transverse to the longitudinal axis 2. In such embodiments, the distance 92 between the center of inner magnet 65 and the center of outer magnets 240 may be adjustable in order to accommodate limbs of varying diameters. For example, the housings 210 may be moved further apart from one another in order to accommodate a limb having a larger diameter, and may be moved toward one another to increase the strength of the magnetic coupling when the limb has a smaller diameter.

In the illustrated form, the outer magnets 240 are fixedly mounted in the housings 210, and rotation of the inner magnet 65 is achieved by rotating the actuating device 200 about the longitudinal axis 2. In other embodiments, the outer magnets 240 may be rotatably mounted in the housings 210. In such forms, rotation of the inner magnet 65 may be achieved by rotating the outer magnets while the actuating device 200 remains stationary, as described, for example, in U.S. Pat. No. 8,777,947 to Zahrly et al, which is hereby incorporated herein by reference in its entirety.

After implantation of IM bone transport nail 1 in a patient, external actuation unit 200 is used at various times, per physician instructions, to non-invasively displace transport carriage assembly 40 as described herein. As will be appreciated, the ability of actuation unit 200 to displace transport carriage assembly 40 against the resistive forces of the bone callus and soft tissue is determined in part by the strength of the magnetic coupling between the inner magnet 65 and the outer magnets 240. For patients with a large limb diameter, the distance 92 between the inner magnet 65 and outer magnets 240 reduces the strength of the magnetic coupling, which limits the amount of torque that can be applied to the threaded rod 55 and inner magnet 65 by the actuation unit 200. The ability of actuation unit 200 to displace transport carriage assembly 40 also depends in part upon the resistive frictional forces internal to the IM bone transport nail 1, such as friction between the engaged threads of threaded rod 55 and threaded block 80.

It is to be understood that the embodiment of the IM bone transport nail 1 represented in FIGS. 1-8 is a preferred embodiment, but other embodiments conforming to the disclosed invention exist and will be able to be produced by a person of ordinary skill in the art. For example, in other embodiments threaded rod 55 may be off-center relative to carriage body 41, and internal chamber 11 and carriage body 41 may have geometries other than housing and cylinder geometries respectively.

In another alternative embodiment (not shown), the orientation of magnet housing assembly 50 is reversed relative to the embodiment depicted in FIGS. 1-8 such that threaded rod 55 extends in the opposite direction from inner magnet 65. A person of ordinary skill in the art will recognize that, in this embodiment, threaded block 80 is affixed to nail body 10 at an axial location closer to proximal end 13 of nail body 10 and that carriage body 41 is positioned distal to threaded block 60 in its entirety, thereby obviating the need for any elongated slot in carriage body 41, and also obviating the need for axial bore 42 and access slot 46. This further enables the use of a significantly shorter carriage body 41 in this embodiment, as transport body 41 need only have a length sufficient to form radially oriented aperture 44 to accommodate transport bone segment screw 45. In this embodiment, rotation of threaded rod 55 to distract middle bone segment 7 will place compressive forces on carriage body 41, magnet housing 70 and the portion of threaded rod 56 that extends between magnet housing 70 and threaded block 80.

Figure 12:
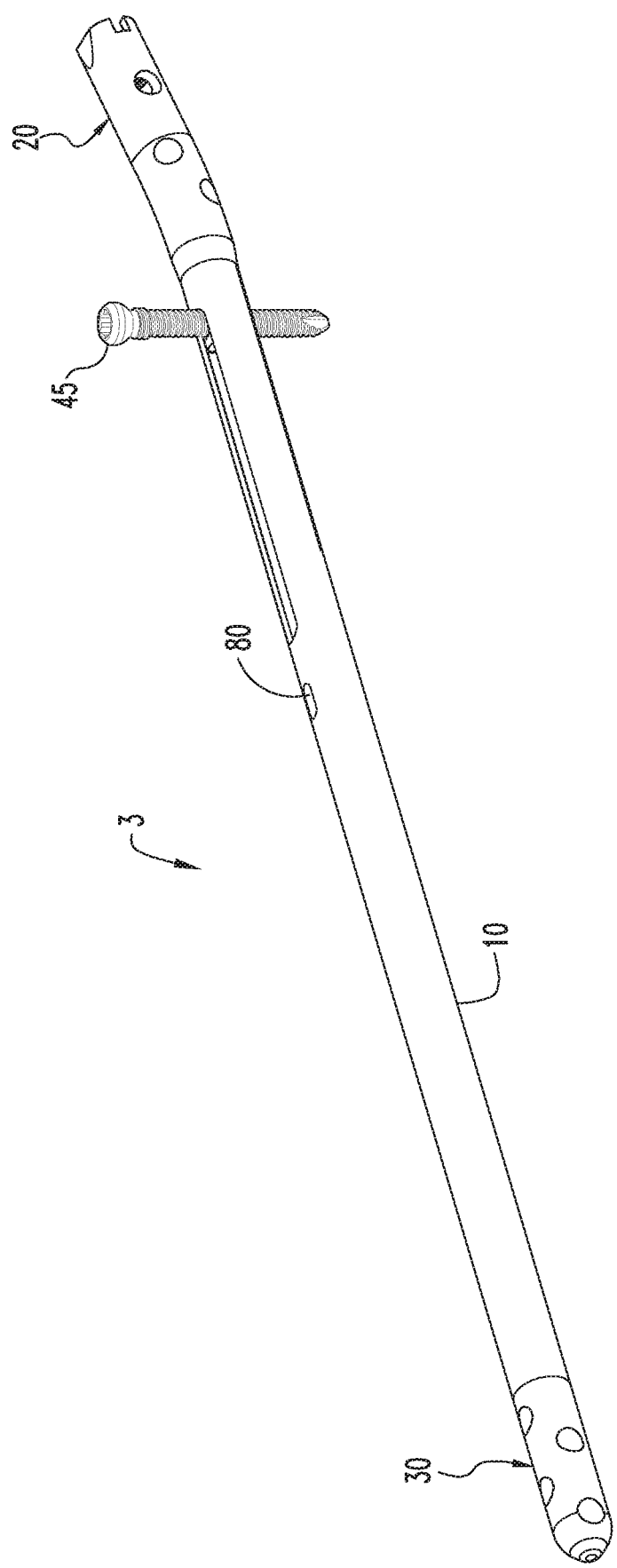
FIG. 12 illustrates an alternate embodiment of an IM bone transport nail in which the nail body is oriented in a reversed position relative to the embodiment depicted in FIG. 1.

Depending on the size of the bone fragments, an opposite assembly of the intramedullary nail may be advisable. For example, FIG. 12 depicts another embodiment that differs from the embodiment depicted in FIGS. 1-8 only in that the orientation of nail body 10 (and the components affixed to or contained therein) is reversed relative to proximal locking portion 20 and distal locking portion 30. While the embodiment depicted in FIGS. 1-8 would advantageously be used to treat proximal femoral or distal tibial defects, as described above, the embodiment depicted in FIG. 12 may be preferred for the treatment of distal femoral or proximal tibial defects. For example, IM bone transport nail 3 depicted in FIG. 12 is well suited for a bone transport procedure to regenerate bone for repair of a distal femoral or proximal tibial defect. When IM bone transport nail 3 is used for repair of a distal femoral defect, first bone fragment 5 is a distal end fragment of a femur and second bone fragment 6 is a proximal end fragment of the femur. When IM bone transport nail 3 is used for repair of a proximal tibial defect, first bone fragment 5 is a proximal end fragment of a tibia and second bone fragment 6 is a distal end fragment of the tibia.

A wide variety of options exist for producing intramedullary nail embodiments having modified features relative to those shown and described herein. For example, it is possible to provide shorter or longer nail bodies and nail bodies having greater or lesser diameters in order to produce intramedullary nails for different bone lengths. Nail body also can have other shapes, such as, for example, in embodiments configured for placement at skeletal locations other than in an intramedullary canal of a long bone. It also can be noted that IM bone transport nail embodiments are envisioned in which rotation of threaded rod 55 is controlled or driven by a mechanism other than a magnetic driver such as magnetic driver 60. Alternative mechanisms for driving threaded rod, for example, can consist of any other driving mechanisms known to a person of ordinary skill in the art, such as an electric motor with or without gear reducer, and a current source inside or outside the patient's body, or a permanent magnet with a gear reducer and a rotating magnetic field source external to the patient. In alternate embodiments, the driving mechanisms can be configured to drive threaded rod 55 in one direction only or in both directions, according to requirements.

As will be appreciated from the descriptions herein and the associated Figures, a wide variety of aspects and embodiments are contemplated by the present disclosure, examples of which include, without limitation, the following:

In one aspect, a bone transport device is provided that includes (i) a main body defining an internal chamber extending along a transport path of the bone transport device, an elongated opening formed in the main body, a first end of the main body configured for fixation to a first bone fragment and a second end of the main body configured for fixation to a second bone fragment; and (ii) a movable transport carriage contained within the internal chamber, the transport carriage configured for fixation to a transport bone fragment. The transport carriage comprises a carriage body and a rotatable driver coupled to the carriage body for axially moving the transport carriage. The rotatable driver comprises a threaded rod and a component operable, upon application of a moving external magnetic field, to cause rotation of the threaded rod. The threaded rod is engaged with internal threads of a threaded block affixed to the main body and the transport carriage is operable, upon rotation of the threaded rod, to translate within the internal chamber relative to the main body. In one embodiment of this bone transport device, rotation of the threaded rod places tension on a portion of the threaded rod extending between the component and the threaded block.

In another aspect, an intramedullary bone transport nail is provided that includes (i) a nail body defining an internal chamber and defining a longitudinally elongated opening along at least a portion of the nail body, (ii) a proximal locking portion defining one or more proximal openings configured to receive one or more proximal fixation elements to fix a proximal end of the intramedullary bone transport nail within a first medullary canal of a first bone fragment; (iii) a distal locking portion defining one or more distal openings configured to receive one or more distal fixation elements to fix a distal end of the intramedullary bone transport nail within a second medullary canal of a second bone fragment; (iv) a transport carriage assembly positioned within the internal chamber; and (v) a threaded block affixed to the nail body and positioned in the elongated slot of the carriage body. The transport carriage assembly includes (a) a carriage body defines an axial bore and a longitudinally elongated slot along at least a portion of the carriage body. The carriage body also defines at least one radially oriented aperture aligned with the elongated longitudinal opening in the nail body, the radially oriented aperture configured to receive a transport bone segment screw; (b) a threaded rod coupled to the carriage body such that the threaded rod is rotatable relative to the carriage body; and (c) a magnetic driver configured to be non-invasively actuated by a moving magnetic field, the magnetic driver coupled to the threaded rod such that rotation of the magnet drives rotation of the threaded rod. The threaded block defines a threaded bore therethrough, through which the threaded rod of the transport assembly is configured to pass in threaded engagement with the threaded bore such that rotation of the threaded rod relative to the threaded block causes relative axial movement between the transport carriage assembly and the nail body to translate the transport carriage assembly axially, relative to the nail body.

In one embodiment, the threaded rod of any other embodiment engages the threaded block at a position along a longitudinal axis of the transport nail between the magnetic driver and the radially oriented aperture. In another embodiment, the threaded rod of any other embodiment places axial tension on a portion of the threaded rod extending between the magnetic driver and the threaded block. In yet another embodiment, at least a portion of the threaded rod of any other embodiment is received within the axial bore of the transport carriage.

In yet another aspect of the present disclosure, an intramedullary bone transport nail is provided that includes: (i) a nail body defining an internal chamber and defining a longitudinally elongated opening along at least a portion of the nail body; (ii) a proximal locking portion defining one or more proximal openings configured to receive one or more proximal fixation elements to fix a proximal end of the intramedullary bone transport nail within a first medullary canal of a first bone fragment; (iii) a distal locking portion defining one or more distal openings configured to receive one or more distal fixation elements to fix a distal end of the intramedullary bone transport nail within a second medullary canal of a second bone fragment; (iii) a transport carriage assembly positioned within the internal chamber; and (iv) a threaded block affixed to the nail body, the threaded block defining a threaded bore therethrough. The transport carriage assembly includes (a) a carriage body defining at least one radially oriented aperture aligned with the elongated longitudinal opening in the nail body, the radially oriented aperture configured to receive a transport bone segment screw; (b) a magnetic driver coupled to the carriage body such that the magnetic driver is rotatable relative to the carriage body; and (c) a threaded rod coupled to the magnetic driver such that rotation of the magnet drives rotation of the threaded rod. The threaded rod of the transport assembly is configured to pass through the threaded block in threaded engagement with the threaded bore such that rotation of the threaded rod relative to the threaded block causes relative axial movement between the transport carriage assembly and the nail body to translate the transport carriage assembly axially relative to the nail body. In another embodiment of this aspect, the magnetic driver is located at a first position along a longitudinal axis of the transport nail between the radially oriented aperture and the threaded block.

In other embodiments, the longitudinally elongated opening of any IM bone transport nail embodiment disclosed herein extends diametrically through the entire nail body for passage of at least one middle bone segment fixing screw that is positioned to affix a transport bone segment to the transport carriage by engaging the transport bone segment at both sides of the nail body. In yet other embodiments, a Herzog bend is provided at one end of the nail of any of the IM bone transport nail embodiments disclosed herein. In still other embodiments, the transport carriage assembly of any IM bone transport nail embodiment disclosed herein is cylindrical in shape. In still yet other embodiments, the elongated slot of any IM bone transport nail embodiment disclosed herein extends diametrically through the entire carriage body and the threaded block extends through the entire carriage body for affixation to the nail body at both sides of the nail body. In other embodiments, the carriage body, the magnetic driver and the threaded rod of any IM bone transport nail embodiment disclosed herein are axially fixed relative to each other as the transport carriage assembly translates by rotation of the threaded rod. In still other embodiments, rotation of the threaded rod of any IM bone transport nail embodiment disclosed herein translates the carriage body, the magnetic driver and the threaded rod relative to the nail body. In yet other embodiments, the magnetic driver of any IM bone transport nail embodiment disclosed herein is rigidly coupled to the threaded rod. In still yet other embodiments, the carriage body, the magnetic driver and the threaded rod of any IM bone transport nail embodiment disclosed herein are coaxial. In other embodiments, the nail body, the carriage body, the magnetic driver and the threaded rod of any IM bone transport nail embodiment disclosed herein are coaxial. In still other embodiments, a total area of threaded engagement between the threaded block and the threaded rod of any IM bone transport nail embodiments disclosed herein remains substantially the same throughout a range of the relative axial movement between the transport carriage assembly and the nail body. In yet other embodiments, the magnetic driver of any IM bone transport nail embodiments disclosed herein comprises a radially poled permanent magnet. In still yet other embodiments, the threaded rod of any bone transport nail embodiments disclosed herein is coupled to the magnetic driver through one or more gear mechanism.

In still another aspect, the present disclosure provides a kit that includes the intramedullary bone transport nail in accordance with any embodiment disclosed herein, two or more bone screws configured to pass through two or more of the proximal openings and the distal openings, and a transport bone segment screw configured to pass through the radially oriented aperture. In another embodiment, the kit further includes one or both of an inserter configured to releasably couple to a proximal end of the intramedullary transport nail or to a distal end of the intramedullary transport nail and alignment instrumentation configured to determine the location of one or more of the proximal openings, the distal openings and the radially oriented aperture such that one or more of the bone screws and the transport bone segment screw may be aligned and inserted.

In still yet another aspect of the present disclosure, there is provided a system that includes (i) an intramedullary bone transport nail in accordance with any embodiment disclosed herein that includes an inner magnet, and (ii) an actuator including at least one outer magnet.

While the invention has been illustrated and described in detail in the drawings and foregoing description, the same is to be considered as illustrative and not restrictive in character, it being understood that only the certain embodiments have been shown and described and that all changes, alternatives, modifications and equivalents that come within the spirit of the inventions are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. An intramedullary bone transport nail, comprising:
 a nail body defining an internal chamber and defining a longitudinally elongated opening along at least a portion of the nail body;
 a first locking portion defining one or more proximal openings configured to receive one or more proximal fixation elements to fix a proximal end of the intramedullary bone transport nail within a first medullary canal of a first bone fragment;
 a second locking portion defining one or more distal openings configured to receive one or more distal fixation elements to fix a distal end of the intramedullary bone transport nail within a second medullary canal of a second bone fragment;
 a transport carriage assembly positioned within the internal chamber, the transport carriage assembly, comprising:
  a carriage body defining an axial bore and a longitudinally elongated slot along at least a portion of the carriage body, the carriage body further defining at least one radially oriented aperture aligned with the elongated longitudinal opening in the nail body, the radially oriented aperture configured to receive a transport bone segment screw;
  a threaded rod coupled to the carriage body such that the threaded rod is rotatable relative to the carriage body;
  a magnetic driver configured to be non-invasively actuated by a moving magnetic field, the magnetic driver coupled to the threaded rod such that rotation of the magnet driver rotates the threaded rod; and
 a threaded block affixed to the nail body and positioned in the elongated slot of the carriage body, the threaded block defining a threaded bore therethrough, through which the threaded rod of the transport assembly is configured to pass in threaded engagement with the threaded bore such that rotation of the threaded rod relative to the threaded block causes relative axial movement between the transport carriage assembly and the nail body to translate the transport carriage assembly axially relative to the nail body;

wherein the transport carriage assembly is cylindrical in shape.

2. The intramedullary bone transport nail of claim 1, wherein the longitudinally elongated opening extends diametrically through the entire nail body for passage of at least one middle bone segment fixing screw that is positioned to affix a transport bone segment to the transport carriage by engaging the transport bone segment at both sides of the nail body.

3. The intramedullary bone transport nail of claim 1, wherein a Herzog bend is provided at one end of the nail.

4. The intramedullary bone transport nail of claim 1, wherein the threaded rod engages the threaded block at a position along a longitudinal axis of the transport nail between the magnetic driver and the radially oriented aperture.

5. The intramedullary bone transport nail of claim 1, wherein the elongated slot extends diametrically through the entire carriage body and wherein the threaded block extends through the entire carriage body for affixation to the nail body at both sides of the nail body.

6. The intramedullary bone transport nail of claim 1, wherein the carriage body, the magnetic driver and the threaded rod are axially fixed relative to each other as the transport carriage assembly translates by rotation of the threaded rod.

7. The intramedullary bone transport nail of claim 1, wherein rotation of the threaded rod translates the carriage body, the magnetic driver and the threaded rod relative to the nail body.

8. The intramedullary bone transport nail of claim 1, wherein the magnetic driver is rigidly coupled to the threaded rod.

9. The intramedullary bone transport nail of claim 1, wherein rotation of the threaded rod places axial tension on a portion of the threaded rod extending between the magnetic driver and the threaded block.

10. The intramedullary bone transport nail of claim 1, wherein the carriage body, the magnetic driver and the threaded rod are coaxial.

11. The intramedullary bone transport nail of claim 1, wherein the nail body, the carriage body, the magnetic driver and the threaded rod are coaxial.

12. The intramedullary bone transport nail of claim 1, wherein at least a portion of the threaded rod is received within the axial bore of the carriage body.

13. The intramedullary bone transport nail of claim 1, wherein a total area of threaded engagement between the threaded block and the threaded rod remains substantially the same throughout a range of the relative axial movement between the transport carriage assembly and the nail body.

14. The intramedullary bone transport nail of claim 1, wherein the magnetic driver comprises a radially poled permanent magnet, and wherein the threaded rod is coupled to the magnetic driver through one or more gear mechanism.

* * * * *